United States Patent [19]

Fanshawe et al.

[11] Patent Number: 5,084,457
[45] Date of Patent: Jan. 28, 1992

[54] BENZOYLAMINOQUINAZOLINONES

[75] Inventors: William J. Fanshawe, Rockland; Joseph W. Epstein, Orange; Jeremy I. Levin, Rockland, all of N.Y.

[73] Assignee: American Cyanamid Company, Stamford, Conn.

[21] Appl. No.: 556,228

[22] Filed: Jul. 23, 1990

[51] Int. Cl.$^5$ .................. A61K 31/505; C07D 239/94
[52] U.S. Cl. .................. 514/257; 514/260; 544/249; 544/287; 544/290
[58] Field of Search .......... 544/289, 290, 249; 514/260, 257

[56] References Cited

U.S. PATENT DOCUMENTS 4,824,469  4/1989  Green et al. .................. 514/260

Primary Examiner—C. Warren Ivy
Assistant Examiner—James H. Turnipseed
Attorney, Agent, or Firm—H. G. Jackson

[57] ABSTRACT

This invention is compounds of the formula:

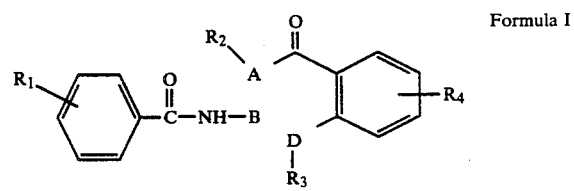

Formula I and a method of treating cognitive and related neuronal behavioral problems in mammals using the compounds.

16 Claims, No Drawings

BENZOYLAMINOQUINAZOLINONES

SUMMARY OF THE INVENTION

This invention is compounds of the formula:

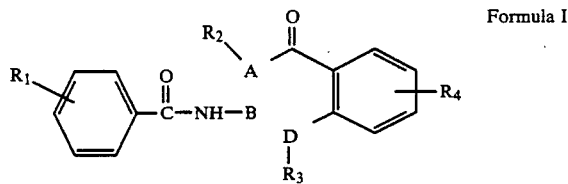
Formula I wherein $R_1$ is hydrogen, alkyl ($C_1$-$C_3$), alkoxy ($C_1$-$C_3$), trifluoromethyl or halogen; $R_2$ is hydrogen, alkyl ($C_1$-$C_6$), or substituted phenyl;

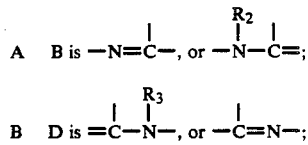

$R_3$ (when it exists) is hydrogen or alkyl ($C_1$-$C_3$); and $R_4$ is hydrogen, halogen, alkyl ($C_1$-$C_3$), mono-or dialkoxy ($C_1$-$C_3$) and —CH=CH—CH=CH— and a method of treating cognitive and related neuronal behavioral problems in mammals using the compounds.

These compound are useful as cognition stimulators in mammals.

In addition, this invention is concerned with new compounds of the above Formula I, with the proviso that when $R_1$ is hydrogen or methoxy, then $R_3$ and $R_4$ may not both be hydrogen; and with the further proviso that when $R_4$ is methyl, then $R_1$ and $R_3$ may not both be hydrogen; and with the still further proviso that when $R_1$ is a methyl group in the 4-position of the phenyl ring, then $R_3$ and $R_4$ may not both be hydrogen.

Certain compounds embraced by Formula I, but eliminated by the provisos, are known in the literature as potential antifungal agents. Their literature citations are given below.

N-(1,4-Dihydro-4-oxo-2-quinazolinyl)benzamide: CA 94(23): 192253V.
$R_1$=H; $R_3$=H; $R_4$=H,

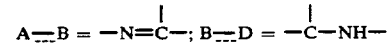

N-(1,4-Dihydro-4-oxo-2-quinazolinyl)-4-methoxybenzamide: CA 94(23): 192253V.
$R_1$=$CH_3O$; $R_3$=H; $R_4$=H;

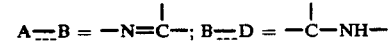

N-(1,4-Dihydro-4-oxo-2-quinazolinyl)-4-methylbenzamide: CA 94(23): 192253V.
$R_1$=4-$CH_3$; $R_3$=H; $R_4$=H;

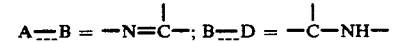

N-(1,4-Dihydro-6-methyl-4-oxo-2-quinazolinyl)benzamide: CA 102(21): 185098d.
$R_1$=H; $R_3$=H; $R_4$=$CH_3$;

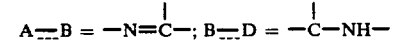

DETAILED DESCRIPTION OF THE INVENTION

The compounds of the present invention may be prepared as set forth in the following reaction scheme.

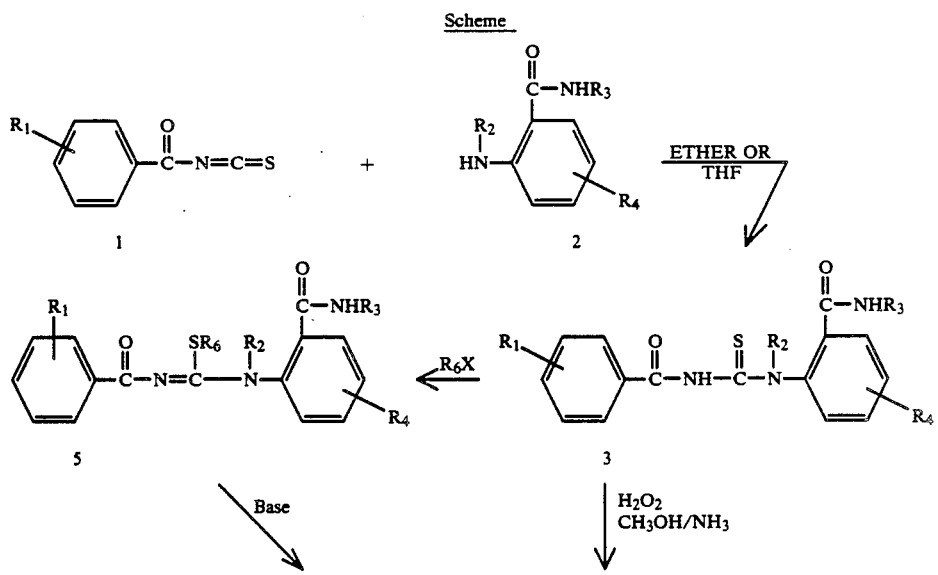

-continued

Scheme

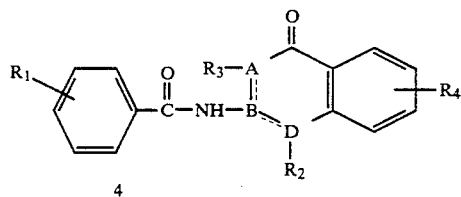

4

In accordance with the above scheme, wherein $R_1$, $R_2$, $R_3$ and $R_4$ are as described above, an aroyl isothiocyanate 1 is reacted with an aminobenzamide 2 in an inert solvent such as ether for several hours, giving an aminocarbonylphenyl thioxomethyl benzamide 3 which is then reacted with hydrogen peroxide in a mixture of an alcohol such as methanol and a base such as ammonia, giving the products 4.

Additionally, 3 can be alkylated with $R_6X$, wherein $R_6$ is methyl or ethyl and X is iodo, bromo or —O—$SO_3R_6$, by either phase transfer conditions using aqueous base, methylene chloride and benzyltrimethylammonium hydroxide or by aqueous base and the alkylating reagent $R_6X$ to give 5 which is in turn converted to 4 using a base, such as sodium hydride in refluxing dioxane or tetrahydrofuran.

The novel compounds of the present invention possess the ability to enhance neuronal function in warm-blooded animals affected by neurologically mediated behavioral problems, including the cognitive deterioration associated with decreased neuronal function which occurs with cerebral insufficiency, aging, dementia and similar conditions.

A useful in vivo test that measures how effectively central nervous system-acting drugs enhance survival in an hypoxic environment, by improving the ratio of energy supply to demand is known as the Hypoxic Survival Test. This test demonstrates the ability of the test compounds relative to a known parasympathomimetic agent physostigmine. This test shows the enhanced survival of test animals in an hypoxic environment after treatment with drug as compared to saline treated control animals without drug. Extensive testing has demonstrated that under conditions of 10% oxygen, only 5–20% of control mice (treated with saline) survive after 5 minutes, whereas 60–80% of the physostigmine treated mice survive. Drugs are tested by intraperitoneal injection into mice 30 minutes prior to placing them in an hypoxic mixture, and then measuring survival. The rationale of this test is that drugs which enhance survival under hypoxic conditions without concomitant, depression or sedative side effects, do so by enhancing energy metabolism, or by preserving normal brain function under conditions of reduced energy metabolism. Given the dependence of the brain on a constant supply of energy, drugs which have this property have many far-reaching therapeutic indications, including recovery from stroke and closed head injury, as well as reducing the deleterious effects of the aging central nervous system. For example, in aged, and in senile demented patients, energy metabolism is known to be deficient, and is thought to contribute significantly to the associated neurochemical and neurophysiological dysfunctions.

Groups of 20 Royal Hart mice (6 weeks of age) are given intraperitoneal injections with test compound (1–200 mg/kg) 30 minutes prior to placing them in an hypoxic mixture (10% oxygen in 90% carbon dioxide) and then survival after 5 minutes is measured.

A separate group of 20 mice is given intraperitoneal injections with saline solution (0.01 ml/g of body weight) and processed as described above.

Still another group of 20 mice is given intraperitoneal injections with 0.125 mg/kg of physostigmine and processed as described above.

Results of this test on representative compounds of the present invention appear in Table I.

TABLE I

| Hypoxic Survival Test | | |
|---|---|---|
| Compound | Dose (mg/kg) | % Survivors |
| N-(1,4-Dihydro-1-methyl-4-oxo-2-quinazolinyl)benzamide | 50 | 60.0 |
| | 100 | 70.0 |
| | 200 | 82.5 |
| N-(1,4-Dihydro-4-oxo-2-quinazolinyl)benzamide | 50 | 65 |
| | 100 | 72.5 |
| | 200 | 70 |
| N-(1,4-Dihydro-1-methyl-4-oxo-2-quinazolinyl)-4-methylbenzamide | 100 | 45 |
| N-(1,4-Dihydro-1-methyl-4-oxo-2-quinazolinyl)-4-methoxybenzamide | 100 | 46.7 |
| N-(1,4-Dihydro-4-oxo-2-quinazolinyl)-4-methoxybenzamide | 10 | 62.5 |
| | 50 | 70 |
| | 100 | 57.5 |
| N-(1,4-Dihydro-4-oxo-2-quinazolinyl)-4-methylbenzamide | 10 | 62.5 |
| | 100 | 57.5 |
| 4-Chloro-N-(1,4-dihydro-4-oxo-2-quinazolinyl)benzamide | 10 | 55 |
| | 50 | 75 |
| | 100 | 70 |
| | 200 | 65 |
| N-(1,4-Dihydro-4-oxo-2-quinazolinyl)-3-methylbenzamide | 10 | 55 |
| | 50 | 70 |
| | 100 | 82.5 |
| | 200 | 75 |
| N-(3,4-Dihydro-3-methyl-4-oxo-2-quinazolinyl)-4-methylbenzamide | 50 | 85 |
| | 100 | 60.0 |
| N-(1,4-Dihydro-6-methyl-4-oxo-2-quinazolinyl)benzamide | 100 | 55 |
| | 200 | 65 |
| N-(3,4-Dihydro-3-methyl-4-oxo-2-quinazolinyl)benzamide | 50 | 65 |
| | 100 | 77.5 |
| | 200 | 60 |
| N-(1,4-Dihydro-6,7-dimethoxy-4-oxo-2-quinazolinyl)benzamide | 100 | 70.0 |
| N-(1,4-Dihydro-4-oxo-2-quinazolinyl)-2-methylbenzamide | 10 | 52.5 |
| | 100 | 50.0 |
| N-(1,4-Dihydro-1-methyl-4-oxo-2-quinazolinyl)-2-methylbenzamide | 100 | 70 |
| N-(3,4-Dihydro-3-methyl-4-oxo-2-quinazolinyl)-2-methylbenzamide | 100 | 37.5 |
| N-(3,4-Dihydro-4-oxo-3-phenyl-2-quinazolinyl)benzamide | 100 | 50 |
| N-(1,4-Dihydro-4-oxobenzo[g]quinazolin-2-yl)benzamide | 10 | 75 |
| | 100 | 40 |

The novel compounds of the present invention have been found to be useful as agents for the treatment of cognitive and related neuronal behavioral problems in mammals when administered in amounts ranging from about 5 mg to about 200 mg/kg of body weight per day. A preferred dosage regimen for optimum results would be from about 10 mg to about 50 mg/kg of body weight per day and such dosage units are employed such that a total of from about 700 mg to about 3.5 g of the active compound for a subject of about 70 kg of body weight is administered in a 24 hour period.

The above described dosage regimen may be adjusted to provide the optimum therapeutic response. A decided practical advantage is that these compounds are both orally as well as parenterally active.

The active compounds may be administered orally, for example, with an inert diluent or with an assimilable edible carrier or they may be enclosed in hard or soft shell gelatin capsules, or they may be compressed into tablets or they may be incorporated directly with the food of the diet. For oral therapeutic administration, these active compounds may be incorporated with excipients and used in the form of tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

Preferred compositions or preparations according to the present invention are prepared so that an oral dosage unit form contains between about 5 and 200 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing these dosage unit forms must be pharmaceutically pure and substantially non-toxic in the amounts used. In addition, these active compounds may be incorporated into sustained release preparations and formulations.

These active compounds may also be administered parenterally or intraperitoneally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The invention will be described in greater detail in conjunction with the following non-limiting examples.

EXAMPLE 1

N-(1,4-Dihydro-1-methyl-4-oxo-2-quinazolinyl)benzamide

To a stirred mixture of 12.0 g of 2-methylaminobenzamide in 300 ml of ether was added dropwise, a solution of 11.8 ml of benzoyl isothiocyanate in 100 ml of ether over 15 minutes. The mixture was stirred overnight, then the solid was collected, giving 22.4 g of N-[[[2-(aminocarbonyl)phenyl]methylamino]thioxomethyl]benzamide.

To a stirred mixture of 16 g of the above benzamide in 180 ml of methanolic ammonia was added dropwise, 12 ml of 30% hydrogen peroxide over 20 minutes. This mixture was stirred overnight, then the solid was collected, dried, partially dissolved in 2 liters of hot acetonitrile and filtered. The filtrate was chilled and the solid was collected, giving 3.8 g of the desired product, mp 252°–253° C. (dec.).

EXAMPLE 2

N-(1,4-Dihydro-4-oxo-2-quinazolinyl)benzamide

To a stirred mixture of 13.6 g of 2-aminobenzamide and 200 ml of ether was added dropwise, a solution of 16.3 g of benzoyl isothiocyanate in 100 ml of ether over 30 minutes. After standing 48 hours the solid was collected, giving 28.4 g of N-[[[2-(aminocarbonyl)phenyl]amino]thioxomethyl]benzamide.

To a stirred mixture of 4.5 g of the above benzamide in a mixture of 120 ml of methanolic ammonia plus 100 ml of methanol, was added dropwise, 3.6 ml of 30% hydrogen peroxide. This mixture was stirred overnight, the solid collected, partially dissolved in 500 ml of hot acetonitrile and filtered. The filtrate was chilled and the solid collected, giving 1.6 g of the desired product as white crystals, mp 227°–228° C. (dec.).

EXAMPLE 3

N-(1,4-Dihydro-1-methyl-4-oxo-2-quinazolinyl)-4-methylbenzamide

To a stirred mixture of 4.5 g of 2-methylaminobenzamide in 200 ml of ether was added dropwise, a solution of 5.6 g of 4-methylbenzoyl isothiocyanate in 100 ml of ether over 20 minutes. After stirring overnight, the solid was collected, giving 8.9 g of N-[[[2-(aminocarbonyl)phenyl]methylamino]thioxomethyl]-4-methylbenzamide.

To a stirred solution of 4.9 g of the above benzamide in 100 ml of methanol plus 100 ml of methanolic ammonia was added dropwise 3.4 ml of 30% hydrogen peroxide. After standing overnight the mixture was filtered, giving 1.5 g of white crystals. These crystals were partially dissolved in 100 ml of hot acetonitrile, filtered and the filtrate chilled, giving 0.371 g of the desired product as white crystals, mp 235°–238° C.

EXAMPLE 4

N-(1,4-Dihydro-1-methyl-4-oxo-2-quinazolyinyl)-4-methoxybenzamide

To a stirred mixture of 8.3 g of 2-methylaminobenzamide and 150 ml of ether was added dropwise, a mixture of 10 g of 4-methoxybenzoyl isothiocyanate in ether over 45 minutes. After stirring overnight, the solid was collected, giving 11.7 g of N-[[[2-(aminocarbonyl)phenyl]methylamino]thioxomethyl]-4-methoxybenzamide.

To a stirred mixture of 0.96 g of the above benzamide and 20 ml of methanol was added 1.0 ml of 30% hydrogen peroxide. A 20 ml portion of methanolic ammonia was added and the mixture was stirred overnight. The reaction was filtered and the filtrate was concentrated giving a tan solid. This solid was partially dissolved in 50 ml of hot acetonitrile and filtered. This filtrate was chilled, giving 0.128 g of the desired product as straw-colored crystals, mp 255°-258° C.

EXAMPLE 5

N-(1,4-Dihydro-4-oxo-2-quinazolinyl)-4-methoxybenzamide

To a stirred mixture of 7.5 g of 2-aminobenzamide and 150 ml of ether was added dropwise, a mixture of 10 g of 4-methoxybenzoyl isothiocyanate in ether over 15 minutes. After stirring overnight the solid was collected, giving 14.2 g of N-[[[2-(aminocarbonyl)phenyl]amino]thioxomethyl]-4-methoxybenzamide.

To a stirred mixture of 9.9 g of the above benzamide, 100 ml of methanolic ammonia and 100 ml of methanol was added 22 ml of 30% hydrogen peroxide. The reaction was cooled because of an exotherm and then stirred overnight at room temperature. The solid was collected, partially dissolved in 800 ml of acetonitrile and filtered. The filtrate was chilled, giving 0.95 g of the desired product as white crystals, mp 235°-236° C. (dec.).

EXAMPLE 6

N-(1,4-Dihydro-4-oxo-2-quinazolinyl)-4-methylbenzamide

To a stirred mixture of 5.4 g of 2-aminobenzamide and 200 ml of ether was added dropwise, a solution of 7.5 g of 4-methylbenzoyl isothiocyanate in 100 ml of ether over 30 minutes. After 48 hours the solid was collected, giving 12.2 g of N-[[[2-(aminocarbonyl)phenyl]amino]thioxomethyl]-4-methylbenzamide.

To a stirred mixture of 9.3 g of the above benzamide, 100 ml of methanolic ammonia and 100 ml of methanol was added dropwise 10 ml of 30% hydrogen peroxide over 3 minutes. When the exotherm subsided to 40° C., 15 ml of 30% hydrogen peroxide was added. The mixture was stirred overnight, the solid collected, partially dissolved in 800 ml of hot acetonitrile filtered and the filtrate chilled, giving 1.4 g of the desirred product as white crystals, mp 238°-239° C. (dec.).

EXAMPLE 7

4-Chloro-N-(1,4-Dihydro-4-oxo-2-quinazolinyl)benzamide

To a stirred mixture of 10.5 g of 4-chlorobenzoyl isothiocyanate in 100 ml of tetrahydrofuran was added a mixture of 6.8 g of 2-aminobenzamide in 200 ml of tetrahydrofuran. After stirring for 3 hours the solid was collected, giving 14.3 g of N-[[[2-(aminocarbonyl)phenyl]amino]thioxomethyl]-4-chlorobenzamide.

To a stirred mixture of 10 g of the above benzamide, 100 ml of methanolic ammonia and 100 ml of methanol was added dropwise 25 ml of 30% hydrogen peroxide, during 10 minutes. The mixture was stirred overnight, the solid was collected, and then partially dissolved in 500 ml of hot acetonitrile. The undissolved solid was collected, mixed with 100 ml of hot water and the solid collected, giving 4.3 g of the desired product as off-white crystals, mp 239°-241° C. (dec.).

EXAMPLE 8

N-(1,4-Dihydro-4-oxo-2-quinazolinyl)-3-methylbenzamide

To a stirred mixture of 7.2 g of 2-aminobenzamide and 200 ml of ether was added dropwise, a solution of 10 g of 3-methylbenzoyl isothiocyanate over 10 minutes. After 48 hours the solid was recovered, giving 14.8 g of N-[[[2-(aminocarbonyl)phenyl]amino]thioxomethyl]-3-methylbenzamide.

To a stirred mixture of 9.3 g of the above benzamide and 200 ml of methanolic ammonia was added dropwise, 10 ml of 30% hydrogen peroxide over 3 minutes. An exotherm required cooling in an ice bath. A 15 ml portion of 30% hydrogen peroxide was added, the mixture was stirred 48 hours, the solid collected, and mixed with 100 ml of hot water. This solid was collected, mixed with 400 ml of hot acetonitrile and filtered. The filtrate was chilled, giving 2.3 g of the desired product as off-white crystals, mp 211°-213° C.

EXAMPLE 9

N-(1,4-Dihydro-1-methyl-4-oxo-2-quinazolinyl)-3-methylbenzamide

To a stirred mixture of 7.97 g of 2-methylaminobenzamide and 200 ml of ether was added dropwise, a solution of 10 g of 3-methylbenzoyl isothiocyanate in ether over 10 minutes. After 48 hours the solid was collected, giving 15.5 g of N-[[[2-aminocarbonyl)phenyl]methylamino]thioxomethyl]-3-methylbenzamide.

To a stirred mixture of 9.8 g of the above benzamide, 100 ml of methanolic ammonia and 100 ml of methanol was added dropwise 5 ml of 30% hydrogen peroxide over 2 minutes. After cooling 5 ml of 30% hydrogen peroxide was added. After further cooling 15 ml of 30% hydrogen peroxide was added and stirring continued overnight at room temperature. The solid was collected, mixed with 250 ml of hot water and this solid collected. This solid was mixed with 400 ml of hot acetonitrile and the solid collected, giving 3.75 g of the desired product as off-white crystals, mp 266°-269° C.

EXAMPLE 10

N-(3,4-Dihydro-3-methyl-4-oxo-2-quinazolinyl)-4-methylbenzamide

To a stirred mixture of 8.0 g of 2-amino-N-methylbenzamide and 200 ml of ether was added dropwise, a solution of 10 g of 4-methylbenzoyl isothiocyanate in 100 ml of ether over 1 hour. After stirring several hours the solid was collected, giving 17.1 g of N-methyl-2-[[[(4-methylbenzolyl)amino]thioxomethyl]amino]benzamide.

To a stirred mixture of 9.8 g of the above benzamide, 100 ml of methanolic ammonia and 100 ml of methanol was added dropwise, 5.0 ml of 30% hydrogen peroxide over 1 minute. After cooling, 5.0 ml of 30% hydrogen peroxide was added, followed by further cooling and addition of 15 ml of 30% hydrogen peroxide. After standing overnight, the solid was collected, then partially dissolved in 500 ml of hot acetonitrile and filtered. The filtrate was chilled, giving 3.7 g of the desired product as white crystals, mp 189°–191° C.

EXAMPLE 11

N-(1,4-Dihydro-6-methyl-4-oxo-2-quinazolinyl)benzamide

To a stirred mixture of 4.5 g of 2-amino-5-methylbenzamide and 200 ml of ether was added dropwise, a solution of 4.9 g of benzoyl isothiocyanate in 100 ml of ether over 20 minutes. After stirring overnight, the solid was collected, giving 8.7 g of 2-[[(benzoylamino)thioxomethyl]amino]-5-methylbenzamide.

To a stirred mixture of 6 g of the above benzamide, 100 ml of methanolic ammonia and 200 ml of methanol was added dropwise, in increments, 20 ml of 30% hydrogen peroxide. After stirring overnight, the solid was collected, partially dissolved in 500 ml of hot acetonitrile and filtered. The filtrate was chilled, giving 1.2 g of the desired product as white crystals, mp 240°–242° C.

EXAMPLE 12

N-(3,4-Dihydro-3-methyl-4-oxo-2-quinazolinyl)benzamide

To a stirred mixture of 12 g of 2-amino-N-methylbenzamide and 200 ml of ether was added dropwise, a solution of 13.1 g of benzoyl isothiocyanate in 100 ml of ether over 30 minutes. The solid was collected, giving 22 g of 2-[[(benzoylamino)thioxomethyl]amino]-N-methylbenzamide.

To a stirred mixture of 9.4 g of the above benzamide, 100 ml of methanolic ammonia and 100 ml of methanol was added dropwise, in increments, 25 ml of 30% hydrogen peroxide. After stirring overnight, the solid was collected, partially dissolved in 500 ml of hot acetonitrile and filtered. The filtrate was chilled, the solid collected and recrystallized from 200 ml of acetonitrile, giving 1.8 g of the desired product as white crystals, mp 185°–187° C.

EXAMPLE 13

N-(1,4-Dihydro-6,7-dimethoxy-4-oxo-2-quinazolinyl)benzamide

To a stirred mixture of 4 g of 2-amino-4,5-dimethoxybenzamide and 200 ml of ether was added dropwise, a solution of 3.3 g of benzoyl isothiocyanate in 100 ml of ether over 15 minutes. After 24 hours the solid was collected, giving 7 g of 2-[[(benzoylamino)thioxomethyl]amino]-4,5-dimethoxybenzamide.

To a stirred mixture of 5.5 g of the above benzamide, 100 ml of methanolic ammonia and 200 ml of methanol was added dropwise, in increments, 25 ml of 30% hydrogen peroxide. After stirring overnight, the solid was collected, partially dissolved in 600 ml of hot acetonitrile and filtered. The filtrate was chilled, giving 2.4 g of the desired product as white crystals, mp 226°–227° C. (dec.).

EXAMPLE 14

N-(1,4-Dihydro-6-methyl-4-oxo-2-quinazolinyl)-4-methylbenzamide

To a stirred mixture of 3 g of 2-amino-5-methylbenzamide and 200 ml of ether was added dropwise, a solution of 3.7 g of 4-methylbenzoyl isothiocyanate in 100 ml of ether over 30 minutes. After 24 hours the solid was collected, giving 6 g of N-[[[2-(aminocarbonyl)-4-methylphenyl]amino]thioxomethyl]-4-methylbenzamide.

To a stirred mixture of 5.2 g of the above benzamide, 100 ml of methanolic ammonia and 100 ml of methanol was added dropwise, in increments, 20 ml of 30% hydrogen peroxide. After stirring 48 hours, the solid was collected, partially dissolved in 400 ml of hot acetonitrile and filtered. The filtrate was chilled, giving 0.5 g of the desired product as white crystals, mp 242°–244° C. (dec.).

EXAMPLE 15

N-(1,4-Dihydro-4-oxo-2-quinazolinyl)-2-methylbenzamide

To a stirred mixture of 4.9 g of 2-aminobenzamide and 200 ml of ether was added dropwise, a solution of 6.67 g of 2-methylbenzoyl isothiocyanate in 100 ml of ether over 15 minutes. After several hours the solid was collected, giving 10.8 g of N-[[[2-(aminocarbonyl)phenyl]amino]thioxmethyl]-2-methylbenzamide.

To a stirred solution of 6.2 g of the above benzamide in 100 ml of methanolic ammonia and 200 ml of methanol was added, in increments, 20 ml of 30% hydrogen peroxide. After standing overnight the solid was collected, partially dissolved in 500 ml of hot acetonitrile and filtered. The filtrate was chilled, giving 0.9 g of the desired product as white crystals, mp 230°–236° C. (dec.).

EXAMPLE 16

N-(1,4-Dihydro-1-methyl-4-oxo-2-quinazolinyl)-2-methylbenzamide

To a stirred mixture of 5.4 g of 2-methylaminobenzamide and 200 ml of ether was added dropwise, a solution of 6.67 g of 2-methylbenzoyl isothiocyanate in 100 ml of ether over 15 minutes. After standing several hours the solid was collected, giving 9.5 g of N-[[[2-(aminocarbonyl)phenyl]methylamino]thioxomethyl]-2-methylbenzamide.

To a stirred mixture of 6.4 g of the above benzamide, 100 ml of methanolic ammonia and 200 ml of methanol was added, in increments, 20 ml of 30% hydrogen peroxide. After standing overnight the solid was collected, partially dissolved in 500 ml of hot acetonitrile and filtered. The filtrate was chilled, giving 2.4 g of the desired product as white crystals, mp 225°–227° C. (dec.).

EXAMPLE 17

N-(3,4-Dihydro-3-methyl-4-oxo-2-quinazolinyl)-2-methylbenzamide

To a stirred mixture of 5.4 g of 2-amino-N-methylbenzamide and 200 ml of ether was added dropwise, a solution of 6.67 g of 2-methylbenzoyl isothiocyanate in 100 ml of ether over 15 minutes. After several hours the solid was collected, giving 11 g of 2-methyl-N-[[[2-

[(methylamino)carbonyl]phenyl]amino]thioxomethyl]-benzamide.

To a stirred mixture of 6.6 g of the above benzamide, 100 ml of methanolic ammonia and 100 ml methanol was added, in increments, 20 ml of 30% hydrogen peroxide. After stirring overnight, the solid was collected, partially dissolved in 500 ml of hot acetonitrile and filtered. The filtrate was chilled, giving 1.5 g of the desired product as white crystals, mp 185°-186° C.

EXAMPLE 18

N-(3,4-Dihydro-4-oxo-3-phenyl-2-quinazolinyl)benzamide

To a stirred mixture of 10 g of 2-amino-N-phenylbenzamide and 500 ml of ether was added dropwise, a solution of 7.7 g of benzoyl isothiocyanate in 100 ml of ether over 20 minutes. After standing several hours the solid was collected, giving 17.3 g of 2-[[(benzoylamino)-thioxomethyl]amino]-N-phenylbenzamide.

To a stirred mixture of 11.3 g of the above benzamide, 150 ml of methanolic ammonia and 250 ml of methanol was added, in increments, 25 ml of 30% hydrogen peroxide. After standing overnight, the solid was collected, partially dissolved in 500 ml of hot acetonitrile and filtered. The filtrate was concentrated and chilled, giving 2.0 g of the desired product as white crystals, mp 185°-188° C.

EXAMPLE 19

N-(1,4-Dihydro-4-oxobenzo[g]quinazolin-2-yl)benzamide

To a stirred mixture of 9.3 g of 3-amino-2-naphthalenecarboxamide and 300 ml of ether was added dropwise, a solution of 8.2 g of benzoyl isothiocyanate in 100 ml of ether over 10 minutes. The solid was collected and crystallized from 1400 ml of hot acetonitrile giving 11.1 g of 3-[[(benzoylamino)thioxomethyl]amino]-2-naphthalenecarboxamide.

To a stirred mixture of 7.0 g of the above carboxamide, 100 ml of methanolic ammonia and 200 ml of methanol was added, in increments, 25 ml of 30% hydrogen peroxide. After stirring overnight the solid was collected, partially dissolved in 500 ml of hot acetonitrile and filtered. The filtrate was chilled, giving 0.9 g of the desired product as cream-colored crystals, mp 240°-242° C. (dec.).

EXAMPLE 20

N-(3,4-Dihydro-3-methyl-4-oxo-2-quinazolinyl)benzamide

To 0.10 g of 2-[[(benzoylamino)thioxomethyl]amino]-N-methylbenzamide in 2.0 ml of N,N-dimethylformamide was added 0.35 ml of 1N sodium hydroxide at 0° C., followed by 0.04 ml of methyl iodide. The solution was stirred and allowed to reach room temperature over 30 minutes. This was diluted with water to give 0.074 g of N-benzoyl-N'-(2-methylaminocarbonylphenyl)carbamimidothioic acid, methyl ester as colorless crystals, mp 193°-195° C. This compound was reacted with sodium hydride in tetrahydrofuran by refluxing for 2½ hours to give N-(3,4-dihydro-3-methyl-4-oxo-2-quinazolinyl)benzamide, mp 185°-187° C.

EXAMPLE 21

N-(3,4-Dihydro-3-isopropyl-4-oxo-2-quinazolinyl)benzamide

To a solution of 26.7 g of 2-amino-N-isopropylbenzamide in 300 ml of tetrahydrofuran was added 24.5 g of benzoylisothiocyanate with stirring. After the exotherm subsided, 200 ml of ethyl ether was added and filtration gave 42.4 g of 2-[[(benzoylamino)thioxomethyl]amino-N-isopropylbenzamide, mp 183°-185° C. To 1.50 g of this compound in 27.5 ml of N,N-dimethylformamide was added 4.80 ml of 1N sodium hydroxide at 0° C. and then 0.55 ml of methyl iodide was added and this was stirred at room temperature for one hour. After the addition of 500 ml of water, the mixture was extracted with three 250 ml portions of ethyl acetate. Evaporation gave 1.55 g of N-benzoyl-N'-(2-isopropylaminocarbonylphenyl)carbamimidothioic acid, methyl ester, mp 117°-120° C. This compound (0.350 g) was dissolved in 35 ml of dioxane and to this was added 0.071 g of 60% sodium hydride/mineral oil dispersion. The mixture was refluxed for 18 hours and then 5% hydrochloric acid was added to pH 2. Addition of 200 ml of water gave a precipitate which was collected and dried to give 0.167 g of the title compound, mp 156°-158° C.

EXAMPLE 22

N-(3,4-Dihydro-3-propyl-4-oxo-2-quinazolinyl)benzamide

To 32.6 g of isatoic anhydride in 150 ml of isopropyl alcohol was added 25 ml of n-propylamine portionwise as the reaction was exothermic. Evaporation of the solution gave 30 g of 2-amino-N-propylbenzamide as colorless crystals, mp 100°-102° C. To a stirred solution of 25.0 g of 2-amino-N-propylbenzamide in 300 ml of tetrahydrofuran was added 22.9 g of benzoylisothiocyanate over 10 minutes. After 2 hours the mixture was diluted with 100 ml of ether and was filtered to give 30.7 g of 2-[[benzoylamino)thioxomethyl]amino]-N-propylbenzamide, mp 172°-174° C. Then, to a solution of 10.2 g of 2-[[benzoylamino)thioxomethyl]amino]-N-propylbenzamide in 100 ml of dichloromethane was added 30 ml of 1N sodium hydroxide to form a two-phase mixture, and to this was added 20 ml of iodomethane and then 4 drops of benzyltrimethylammonium hydroxide solution. After stirring for 3 hours, the organic phase was separated and dried over anhydrous sodium sulfate. Filtration and evaporation of the filtrate gave 9.4 g of N-benzoyl-N'-(2-propylaminocarbonylphenyl)carbamimidothioic acid, methyl ester, mp 86°-89° C. To a solution of 7.10 g of this compound in 300 ml of anhydrous dioxane was added 1.45 g of 60% sodium hydride in mineral oil suspension and the mixture was refluxed for 5 hours. The reaction mixture was then poured into 1.5 liter of water and made acidic with hydrochloric acid. The crystals that formed were collected and recrystallized from ethyl acetate-hexane to give N-(3,4-dihydro-3-propyl-4-oxo-2-quinazolinyl)benzamide as colorless crystals, mp 133°-135° C.

We claim:

1. A compound of the formula:

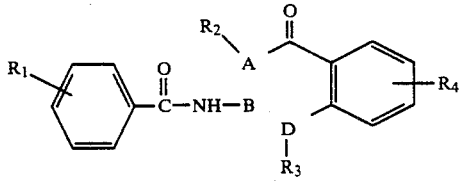

wherein $R_1$ is hydrogen, alkyl($C_1$-$C_3$), alkoxy($C_1$-$C_3$), trifluoromethyl or halogen; $R_2$ (when it exists) is hydrogen, alkyl($C_1$-$C_6$), or phenyl;

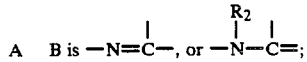

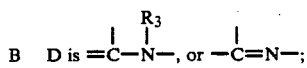

$R_3$ (when it exists) is hydrogen or alkyl($C_1$-$C_3$); $R_4$ is hydrogen, halogen, alkyl($C_1$-$C_3$); mono-or dialkoxy($C_1$-$C_3$) or —CH=CH—CH=CH—; with the proviso that when $R_1$ is hydrogen or methoxy, then $R_3$ and $R_4$ may not both be hydrogen; with the further proviso that when $R_4$ is methyl, then $R_1$ and $R_3$ may not both be hydrogen; and with the still further proviso that when $R_1$ is a methyl group in the 4-position of the phenyl, then $R_3$ and $R_4$ may not both be hydrogen.

2. The compound according to claim 1, N-(1,4-dihydro-1-methyl-4-oxo-2-quinazolinyl)benzamide.

3. The compound according to claim 1, N-(1,4-dihydro-1-methyl-4-oxo-2-quinazolinyl)-4-methylbenzamide.

4. The compound according to claim 1, 4-chloro-N-(1,4-dihydro-4-oxo-2-quinazolinyl)benzamide.

5. The compound according to claim 1, N-(1,4-dihydro-4-oxo-2-quinazolinyl)-3-methylbenzamide.

6. The compound according to claim 1, N-(3,4-dihydro-3-methyl-4-oxo-2-quinazolinyl)-4-methylbenzamide.

7. The compound according to claim 1, N-(3,4-dihydro-3-methyl-4-oxo-2-quinazolinyl)benzamide.

8. The compound according to claim 1, N-(1,4-dihydro-1-methyl-4-oxo-2-quinazolinyl)-2-methylbenzamide.

9. The compound according to claim 1, N-(3,4-dihydro-3-methyl-4-oxo-2-quinazolinyl)-2-methylbenzamide.

10. The compound according to claim 1, N-(3,4-dihydro-4-oxo-3-phenyl-2-quinazolinyl)benzamide.

11. The compound according to claim 1, N-(1,4-dihydro-4-oxobenzo[g]quinazolin-2-yl)benzamide.

12. The compound according to claim 1, N-(3,4-dihydro-3-methyl-4-oxo-2-quinazolinyl)benzamide.

13. The compound according to claim 1, N-[3,4-dihydro-3-(1-methylethyl)-4-oxo-2-quinazolinyl]benzamide.

14. The compound according to claim 1, N-(3,4-dihydro-4-oxo-3-propyl-2-quinazolinyl)benzamide.

15. A method of treating cognitive and related neuronal behavioral problems in a mammal, which comprises administering internally to said mammal a cognition stimulating amount of a compound of the formula:

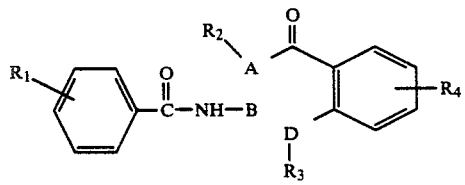

wherein $R_1$ is hydrogen, alkyl($C_1$-$C_3$), alkoxy($C_1$-$C_3$), trifluoromethyl or halogen; $R_2$ is hydrogen, alkyl($C_1$-$C_6$), or phenyl;

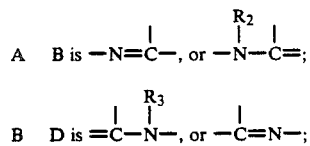

$R_3$ (when it exists) is hydrogen or alkyl($C_1$-$C_3$); $R_4$ is hydrogen, halogen, alkyl($C_1$-$C_3$), mono-or dialkoxy($C_1$-$C_3$) or —CH=CHCH=CH—.

16. A cognition stimulating composition of matter in dosage unit form, comprising from about 25 to about 500 mg of a compound of claim 12 in association with a pharmaceutically acceptable carrier.

* * * * *